United States Patent [19]

Barnes

[11] Patent Number: 4,761,752

[45] Date of Patent: Aug. 2, 1988

[54] FRACTIONAL STEP CORRELATOR

[75] Inventor: Casper W. Barnes, Newport Beach, Calif.

[73] Assignee: North American Philips Corporation, New York, N.Y.

[21] Appl. No.: 854,260

[22] Filed: Apr. 21, 1986

[51] Int. Cl.$^4$ ............................................. G06F 15/336
[52] U.S. Cl. ............................................. 364/728
[58] Field of Search ............... 364/728, 724; 342/189; 382/42

[56]  References Cited

U.S. PATENT DOCUMENTS

| 4,283,767 | 8/1981 | Rountree | 364/728 X |
| 4,460,890 | 7/1984 | Busby | 364/724 X |
| 4,562,312 | 12/1985 | Duttweiler | 364/728 X |
| 4,604,720 | 8/1986 | Stikvoort | 364/724 |

Primary Examiner—David H. Malzahn
Attorney, Agent, or Firm—Jack E. Haken

[57] ABSTRACT

A circuit for determining the cross-correlation function between two digitally sampled signals comprises a plurality of fractional step delay (FSD) digital interpolation filters which estimate the value of one of said input signals at intervals between said samples and a plurality of correlation circuits each of which determines the correlation between the first signal and the output of one of said interpolation filters.

7 Claims, 8 Drawing Sheets

FRACTIONAL STEP CORRELATOR

The invention is a correlation circuit for use with discrete-time, digital signals. The invention comprises the combination of a fractional-step delay (FSD) digital interpolation filter and a discrete-time digital correlator. The invention is useful, for example, in systems which measure the velocity of ultrasound scatterers using pulse-echo techniques.

BACKGROUND OF THE INVENTION

In pulse-echo ultrasound investigations, the velocity of ultrasound scatterers can be estimated from the relative time delay between signals in successive A-lines. This relative time delay can be determined from the value of a time lag which maximizes the cross-correlation of signals from two successive A-lines.

If the ultrasound scatterers have low velocity, the relative time delay between the signals in successive A-lines may be much shorter than the pulse repetition rate of the ultrasound transmitter (that is: the time interval between signal samples). Conventional discrete time correlators only generate correlation estimates for time lags which are multiples of the signal sample interval. Thus, when the scatterer velocity is low, it is difficult to accurately locate the maximum of the cross-correlation function from cross-correlation samples that are spaced at multiples of the sample interval. This problem is particularly severe if the cross-correlation estimates are computed with one-bit correlators.

DESCRIPTION OF THE PRIOR ART

The use of correlation functions makes it possible to measure time delays between signals as described, for example, in the article "The Generalized Correlation Method for Estimation of Time Delays", C. H. Knapp and G. C. Carter, IEEE Transactions on Acoustics, Speech, and Signal Processing, Vol. ASSP-24, No. 4, 1976 which is incorporated herein, by reference, as background material.

French patent application Serial No. 85 17 851, filed Dec. 3, 1985 describes an instrument (FIG. 11) for producing images of fluid flow within a body by ultrasound pulse-echo techniques (especially of blood-flow in organs such as the heart). It comprises at least one ultrasound transducer 10 associated with a pulse generator which generates a periodic pulsed signal at a pulse repetition frequency $$F = \frac{1}{T}.$$

The transducer 10 is connected to a transmitter stage 20, a reception and signal processing stage 30, and a device 40 that effects mechanical scanning of the transducer. The transmitter stage comprises a generator of electrical excitation signals that are sent toward the transducer which converts them into periodic pulse trains of ultrasound energy. This emission is commanded by clock signals at the predetermined frequency F—on the order of, for example 5 kHz—by a sequencer comprising, an oscillator having a frequency of, for example, 32 megahertz, and a frequency divider. The divider delivers clock signals as well as other command signals to connections 104 and 106 respectively, at 1 kilohertz and 16 megahertz in the example described here. A T-R switch prevents the blinding of the reception circuits by the emission signals.

The reception and processing stage 30 comprises, at the output of the T-R switch, a high-frequency amplifier 300 (which includes means for compensation of gain as a function of the depth) followed by two parallel signal processing channels 301 and 302. Channel 301 is the conventional type, and comprises, in series, an envelope detector 310, a logarithmic compression amplifier 311, a storage and scanning conversion device 370 (which also includes a color coding function), and a display device 312. This channel 301 forms images of the media explored, in a gray scale, based on the principles of classic echography.

Channel 302 comprises, in series, a fixed echo suppression circuit 320, a flow parameter estimation circuit 330, a discriminator circuit 360, the storage, scanning conversion and color coding device 370, and the display device 312.

In FIG. 12 the digital fixed-echo suppression circuit 320 comprises an analog-digital converter 321 whose output is connected directly to the negative input of a subtractor 322 and through a delay circuit 323 to the positive input of the same subtractor. The delay of circuit 323 can be equal to T. Circuit 320 eliminates all fixed echoes, especially those caused by the reflection of the ultrasound energy from the walls of the vessels which contain the flows under study. Fixed echoes are annoying due to their much higher amplitude (on the order of +40 dB in the case of blood flows) than the working signals which are back-scattered by moving targets. Circuit 320 is commanded, through connection 106, by the frequency divider of the sequencer that provides it with the sampling command signal at the 16 MHz frequency.

FIG. 13 shows the flow parameter estimation circuit 330. It comprises correlation circuits and an interpolation circuit. On the basis of the difference between two successive echographic A-lines of samples $d_i(t)$, $d_{i+1}(t)$, etc. . . . (where i represents the index of this signal) successively furnished by the fixed echo suppression circuit 320, the correlation circuit delivers an odd number (2I + 1) of correlation function values. The interpolation circuit thus delivers parameters which characterize the various flows encountered along the axis of propagation of the ultrasonic wave on the basis of these values. These parameters are here the axial components of the average local speed $V_Z$ and the local variance $\sigma^2$ of the latter, ("local" here being used in the sense of the localization in depth along the axis of propagation.)

The correlation circuit 330 comprises (2I + 1) correlators 342 which directly receive the output $d_{i+1}(t)$ of fixed echo suppression circuit 320 and, at a second input, receive this same output delayed by delays 341 and therefore corresponding to the preceding signal $d_i(t)$. Furthermore, each of delays 341 has a distinct delay which assumes (2I + 1) values from $T - I \Delta t$ to $T + I \Delta t$, where $\Delta t$ is the sampling interval to permit computing the (2I + 1) values of the correlation function. This parallel computation of the (2I + 1) values of the correlation function uses K successive samples of the two input signals of the correlators. The groups of K samples define successive time windows of length $K\Delta t$ offset gradually at the cadence of the frequency imposed by connection 106. The correlation function is defined by an expression of the type:

$$f_i(J,P) = \sum_{k=1}^{k=K} d_i((k + J)\Delta t) \cdot d_{i+1}((k + J + P)\Delta t) \quad (1)$$

in which:

J determines the start of the time window of length $K\Delta t$,

P is the time delay introduced between $d_i$ and $d_{i+1}$ ranging from $-I$ to $+I$, i is the rank of the difference between two successive echographic lines $e_i$ and $e_{i+1}$.

The correlators 342, commanded through output connection 106 of the frequency divider 23 of the sequencer, are preferably 1-bit correlators (for example type TDC 1023 made by TRW, La Jolla CA 92038). When the embodiment described comprises these 1-bit correlators, the interpolation circuit 350 is then, in general, a linear interpolation circuit.

The interpolation circuit can be a programmed microprocessor, or preferably a wired computer unit. This interpolation circuit works as follows: in a first stage there
is a search for the maximum value among the $(2I+1)$ values of the correlation function, the two adjacent correlation function values are associated with it, and these three values permit the reconstitution of the principal correlation peak, in isoceles form. The abscissa $\pi(J)$ of the principal peak of correlation gives access to the local speed $V_Z$ at depth $$Z_o = \frac{cJ\Delta t}{2} \quad (2)$$

by multiplication according to the formula:

$$V_z(Z_o) = c \cdot \frac{\pi(J)}{2T} \quad (3)$$

and the amplitude $f_{MAX}$ of this peak gives access to the variance $\sigma^2(z_o)$ by operating according to the formula:

$$\sigma^2(z_o) = A\left(1 - \frac{f_{MAX}(J)}{K}\right) \quad (4)$$

where A is a factor of proportionality.

Between each of the correlators 342 and the corresponding inputs of the interpolation circuit 350 there is an average computing circuits (which are in fact accumulators), each comprising an adder 344 and a delay line 345 with a delay T. These average computing circuits permit the accumulation of the correlation function values on N successive A-lines, and to find their average. The adders 344 and the delay lines 345 are connected to the sequencer by connection 104 to be reset to zero at regular $(N\times T)$ intervals.

The output signals from the flow parameter estimation circuit 330 are then validated by a discriminator circuit 360. The values thus confirmed are sent toward the display device 312 by means of color coding device 370.

The presence of the discriminator circuit 360 is essential. Outside of flow zones the output signal from fixed echo suppression signal 320 is noise and the output of the flow parameter estimation circuit 330, which processes this noise, is not an indication of a zero speed. Circuit 360 (FIG. 14) therefore comprises, in series, a multiplier 361 which receives and squares the output signal $d_i$ from the fixed echo suppression circuit 320; a summor 362 which computes the local energy of this difference signal according to the formula:

$$E_i(J) = \sum_{k=1}^{k=K} d_i^2((k + J)\Delta t); \quad (5)$$

a circuit (364, 365) which computes the average of the local energy on N shots, (as in the case of circuits 344 and 345 it is an accumulator comprising an adder 364 and a delay line 365 of delay T), that is to say $(N-1)$ differences according to the expression:

$$E(J) = \sum_{i=1}^{i=N-1} E_i(J). \quad (6)$$

The average value computer is followed by a validation circuit which comprises a comparator 461 which receives the output from the accumulator and a reference voltage forming a threshold. The output from the comparator is the logic level 0 or 1 depending on whether the voltage from the accumulator below or above the reference threshold. Two multipliers 463 and 464 receive, respectively, the output signals from circuit 330 at their first input, transmit these two signals, hereinafter $V'_Z$ and $\sigma'^2$ at their respective outputs or simply transmit zero values depending on whether the validation signal delivered at their second input by comparator 461 is respectively 1 or 0. Outside the true flow zones, the average energy computed at the output from circuit is that of noise alone, and can be measured in the absence of excitation, to determine the appropriate value of the threshold. In the presence of signals backscattered by the moving targets, the average energy of the signal $d_1$ is higher than that of the noise alone; this validates signals delivered by flow parameter estimation circuit 330.

The two outputs of the discriminator circuit 360 are sent towards the storage, scanning conversion and color coding device 370.

The implementation and use of fractional-step delay (FSD) digital filters is described in the article "State Space Realization of Fractional-Step Delay Digital Filters with Applications to Array Beam Forming", Shu-Hung Leung and Casper W. Barnes, IEEE Transactions on Acoustics, Speech, and Signal Processing, Vol. ASSP-32, No. 2, April 1984, pages 371-380 which is incorporated herein, by reference, as background material.

SUMMARY OF THE INVENTION

The above-mentioned difficulty in the application of correlation techniques to determine flow from ultrasound A-line signals is overcome by the use of fractional step correlators which are implemented using fractional step delay (FSD) interpolation filters. Fractional step delayed signal estimates are correlated, using one-bit correlators, to locate the maximum of the cross-correlation function of the A-line signals. Fractional step correlators are relatively simple devices which are implemented with the full desired signal precision, that is 8, 12 or 16 data bits. Once fractional step delay estimates have been generated using the FSD filters, the cross-correlations of the full precision data can be efficiently computed with the data limited to one-bit.

When using FSD digital filters, the complexity of hardware used to implement an ultrasound velocity measuring scanner can be reduced if the A-line signal is interpolated prior to correlation (in contrast to the prior art which utilized hardware to interpolate the cross-correlation function). The multiplications required for the FSD filters can be efficiently implemented by a table look-up using ROMs.

DESCRIPTION OF THE DRAWINGS

The description of the prior art and present invention is made with reference to the appended drawings in which.

DESCRIPTION OF THE PREFERRED EMBODIMENT

FSD Digital Interpolation Filter

Let $X(n\pi)$ denotes digital samples of a signal taken with a sample period $\pi$. The signal values between sample times can be approximated by using an appropriate interpolating function in the following form:

$$\begin{aligned} X(t) &= \sum_n X(n\tau) g(t - n\tau) \\ &= \ldots + X(-2\tau)g(t + 2\tau) + x(-\tau)g(t + \tau) + \\ &\quad x(0)g(t) + x(\tau)g(t - \tau) + \ldots \end{aligned} \quad (7)$$

where g(t) is an interpolating function.

Figure 1:
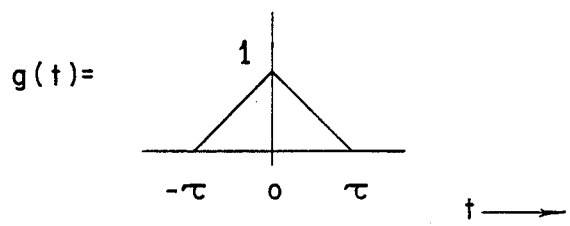
FIG. 1 represents a linear interpolation function.
Figure 2:
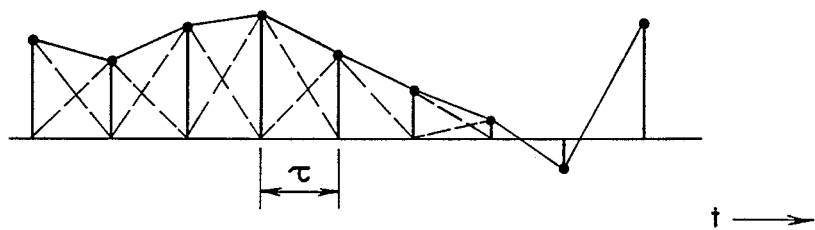
FIG. 2 represents the application of the function of FIG. 1 to interpolate a signal.

FIG. 1 illustrates a linear interpolating function g(t) which has values of 0 for a $t = \pm\pi$ and a value of 1 for $t=0$. In this case the interpolated function comprises a series of straight line approximations as illustrated in FIG. 2.

The linear interpolating function of FIG. 1 requires infinite bandwidth. For band limited interpolation let $$g(t) \frac{\text{SIN}(\pi t/\tau)}{t/\tau} = \text{sinc}(t/\tau) \quad (8)$$

Figure 3:
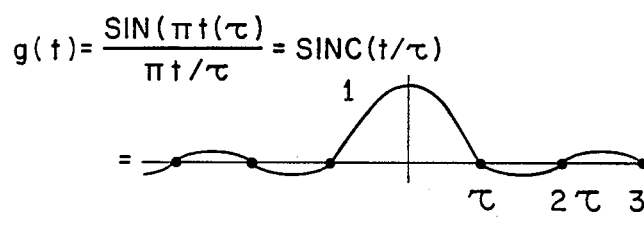
FIG. 3 represents a sinc interpolation function.
Figure 4:
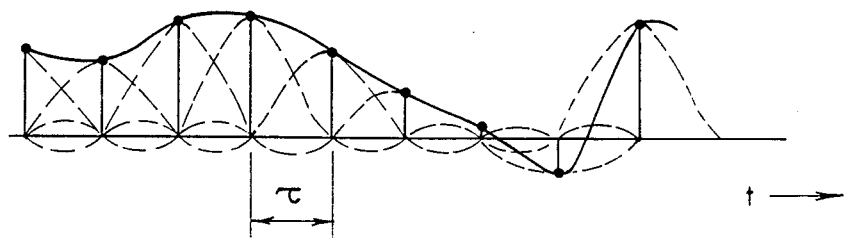
FIG. 4 represents the application of the function of FIG. 3 to interpolate a signal.

In this case the interpolating function g(t) has the form illustrated in FIG. 3 and the interpolated signal will have the form illustrated in FIG. 4.

A time delay interpolator can be constructed by taking samples of x(t) with sample period $\pi$ and with sample times that are offset by a fraction of $\pi$ from the original samples; that is $$y(m\pi) = x(m\pi - \xi) \quad (9)$$

where $$0 < \xi < \pi. \quad (10)$$

These samples can be obtained from the interpolated signal using equation 11:

$$y(m\tau) = x(m\tau - \xi) = \sum_n x(n\tau)g(m\tau - n\tau - \xi) \quad (11)$$

Let $$h_\xi(n) = g(n\tau - \xi) \quad (12)$$

then $$y(m\tau) = \sum x(n\tau) h_\xi(m - n) = \sum h_\xi(n)x(m\tau - n\tau) \quad (13)$$

Thus, the interpolated samples can be obtained from the original samples by a discrete convolution which represents a time-invariant filtering operation $$y(n\pi) = x(n\pi) * h(n) \quad (14)$$

where h(n) is the unit pulse response of the interpolating filter.

To ensure that h(n) is finite and causal, it may be necessary to truncate the interpolating function and to introduce a delay $K\pi$; thus, in practice the interpolating filter should compute $$y(m\pi) = x(m\pi - K\pi - \xi) \quad (15)$$

where K is a positive integer chosen to be sufficiently large so that $$g(n\pi - K\pi - \xi) = 0 \text{ for } n < 0. \quad (16)$$

Thus the filtering operation for the time delay interpolator is $$\begin{aligned} y(m\tau) &= x(m\tau - k\tau - \xi) \\ &= \sum_{n=0}^{N-1} h_\xi(n)x(n\tau - m\tau) \end{aligned} \quad (17)$$

where $$h_\xi(n) = g(n\tau - K\tau - \xi). \quad (18)$$

Figure 5:
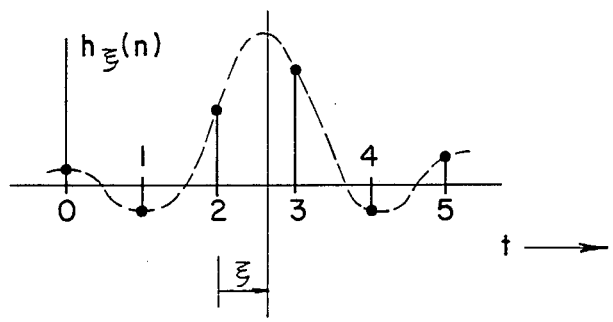
FIG. 5 represents the truncated, delayed unit pulse response of a sinc (k $(\pi)$) filter.
Figure 6A:
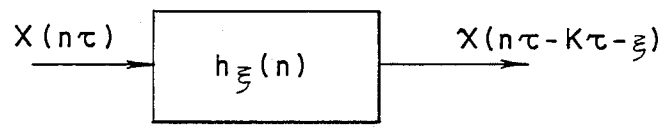
FIGS. 6A and 6B are alternate block diagram representations of the interpolator.
Figure 6B:
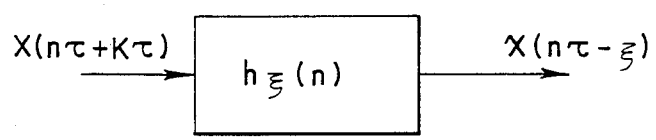

FIG. 5 illustrates the truncated pulse response of a sinc $(K\pi)$ interpolator for the case n=6 and K=2. FIG. 6a and 6b are alternate representations of the transfer function of such an interpolator.

Figure 7:
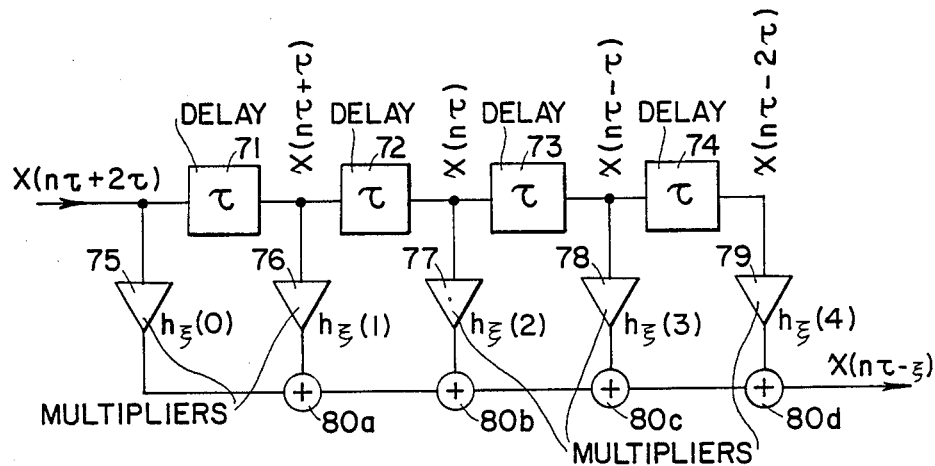
FIG. 7 is a fractional step-delay digital filter using a transversal filter architecture.

FIG. 7 illustrates the implementation of the FSD filter using a conventional transversal filter architecture with n=5. The input signal 70 passes through cascade delay elements 71, 72, 73, and 74 each having a delay period $\pi$. The delay cascade is tapped and signals from the successive delays are multiplied by factors h (0), h (1), h (2), h (3), and h (4) in multipliers 75, 76, 77, 78, and 79 respectively. The output signals from the multiplier 75 through 79 are summed in adding circuits 80a, 80b, 80c, and 80d to produce the filter output. The multiplying factors are calculated using equations 17 and 18 and standard digital filter design techniques as described in the above-mentioned background references. The FSD filter is typically constructed to match the precision of the input signal, for example 8, 12, or 16-bit data. For 8 or 12-bit data the multipliers can be efficiently implemented by table look-up with ROMS.

Discrete-Time Correlators

Figure 8:
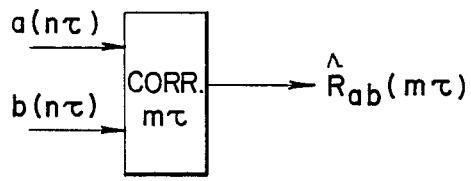
FIG. 8 is a block diagram of a correlation estimator.
Figure 9:
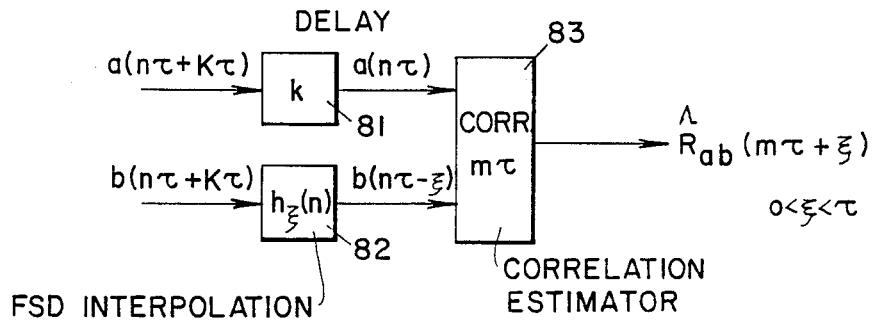
FIG. 9 is a fractional step correlation estimator.

The cross-correlation between two discrete-time signals, $a(n\tau)$ and $b(n\tau)$, can be estimated from time averages of the form $$R_{ab}(m\tau) = C \sum_n a(n\tau + m\tau) b(n\tau) \quad (19)$$

where the sum is taken over a finite number of terms and C is an appropriate normalizing constant. A discrete correlation estimator can be represented in block diagram form as shown in FIG. 8. FIG. 9 illustrates a fractional step correlation estimator. A first signal $a(n\tau + K\pi)$ is passed through a constant delay circuit 81 with delay time K. The second input signal $b(n\pi + K\pi)$ is passed through FSD interpolation filter 82 with transfer function h (n). The outputs of circuits 81 and 82 are applied to inputs of a discrete time correlation estimator 83 the magnitude of whose output is an estimate of the cross-correlation between the signals $a(n\pi)$ and $b(n\pi -)$.

Figure 10A:
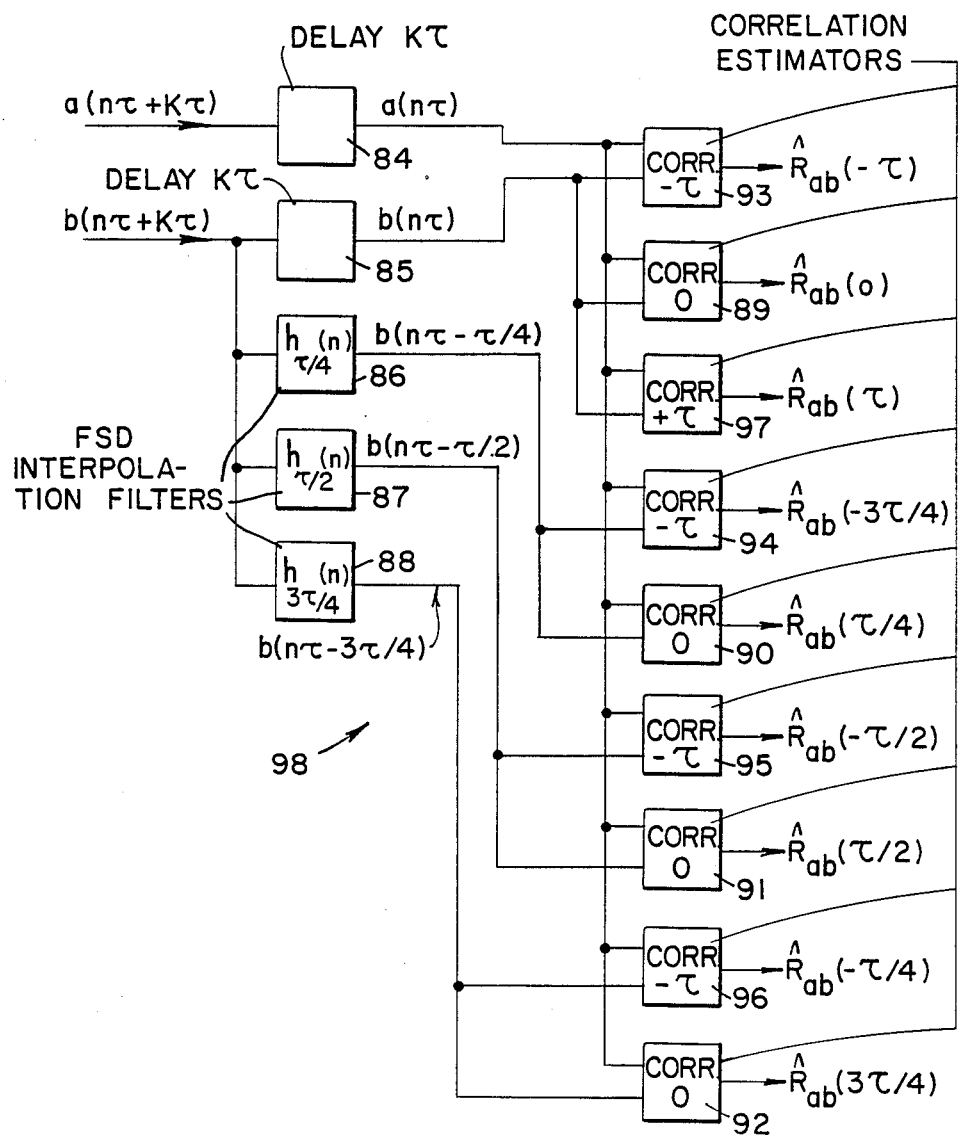
FIG. 10A is a fractional step cross-correlator.

FIG. 10a is a fractional step cross-correlator 98 of the present invention. A first signal $a(n\pi + K\pi)$ is applied to a first input of a fixed delay circuit 84 having a delay time $K\pi$. The second input signal $b(n\pi + K\pi)$ is applied to the input of a second delay circuit 85 which is identical to the delay circuit 84. The second input signal is also applied to the inputs of three FSD interpolation filters 86, 87, and 88 having, for example, respective delay times of $\pi/4$, $\pi/2$, and $3\pi/4$. The output of delay circuit 84 is separately correlated with the output of delay circuit 85 and with the outputs of the fractional step interpolation filters 86, 87, and 88 in discrete time correlation estimator circuits 89, 90, 91 and 92 whose estimates respectively represent the cross-correlation of the input signals at times 0, $\pi/4$, $\pi/2$, $3\pi/4$. The same inputs are respectively applied to discrete time correlation estimators 93, 94, 95 and 96 which are constructed to cross-correlate signals spaced by sample interval $-\pi$ and whose outputs respectively represent estimates of the cross-correlation of the signals at period and $-\pi$, $-3\pi/4$, $-\pi/2$, and $-\pi/4$. The outputs of delay circuits 84 and 85 are further applied to a single discrete time correlation estimator 97 having an integral delay of $\pi$ whose output is an estimate of the correlation of the input signals at time $\pi$. The respective outputs of the correlation estimators 89–96 represent the cross-correlation function of the input signals.

FSD filters can be designed to produce fractional step delays with any value between zero and $\pi$. For example, for higher resolution delay estimates one could use N-1 FSD filters with delays of $k\pi/N$, $k=1, 2, 3, \ldots$, N-1, for any N. Also, the fractional step delays need not be equally spaced, although this is probably most desirable for a blood flow estimator.

Figure 11:
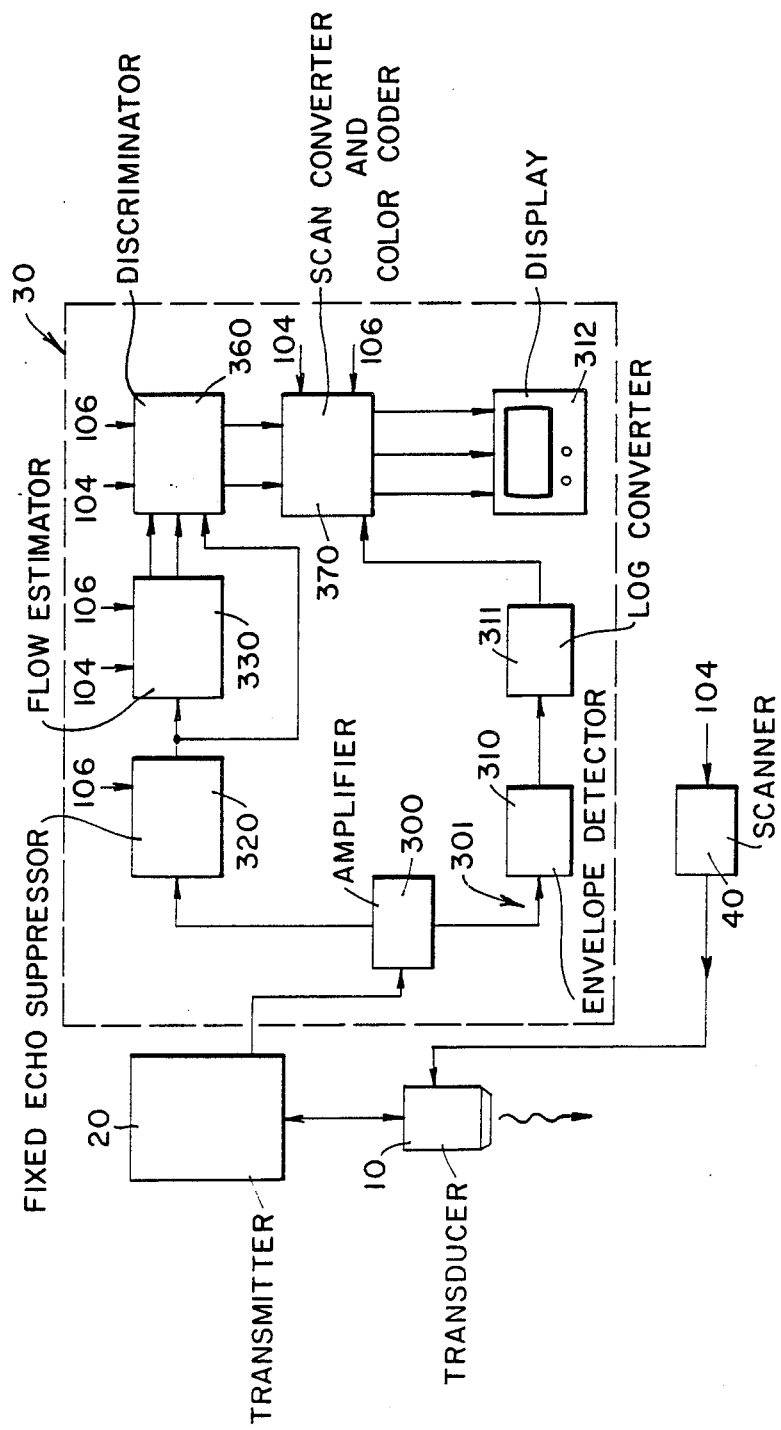
FIG. 11 is an ultrasound, time domain flow imaging scanner of the prior art.
Figure 10B:
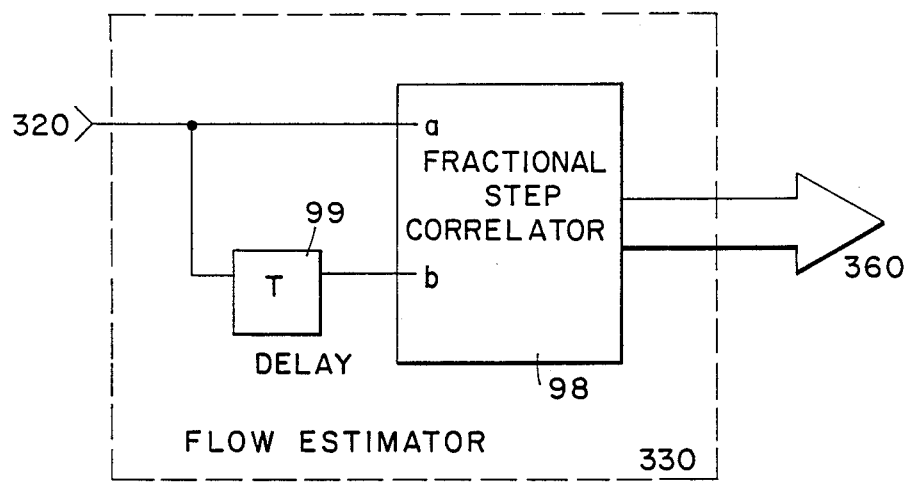
FIG. 10B illustrates the application of the correlator of FIG. 10A to ultrasound flow imaging.
Figure 12:
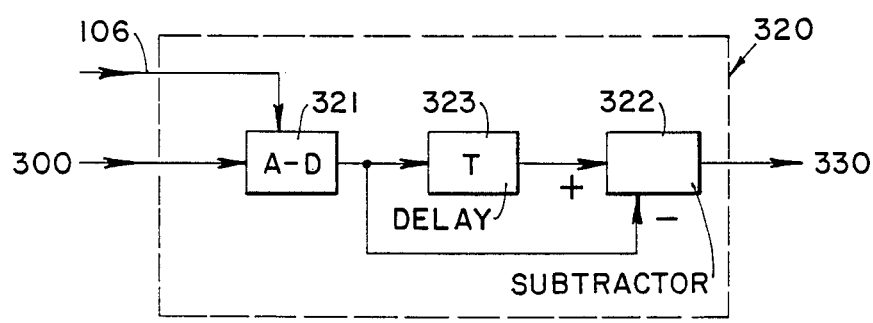
FIG. 12 is a fixed echo suppressor of the prior art.

FIG. 10b illustrates the application of the fractional step correlator in a flow estimator 330 for use in the prior art ultrasonic pulse echo flow measuring device of FIG. 11. The output of the fixed echo suppressor 320 is applied to the first input of a fractional step correlator 98 and to the input of a fixed delay 99 having a delay period T equal to the pulse repetition period of the ultrasound transmitter 20. The output of the delay 98 is applied to the second input of the fractional step correlator 98 so that the respective inputs of the fractional step correlator represents successive ultrasound echo A-lines with fixed echoes suppressed. The output signals from the correlation estimators in the fractional step correlator 98 are applied, through the discriminator 360 and the scan converter and color coder 370 to determine the color of regions in the display 312, as in the prior art scanner.

Figure 13:
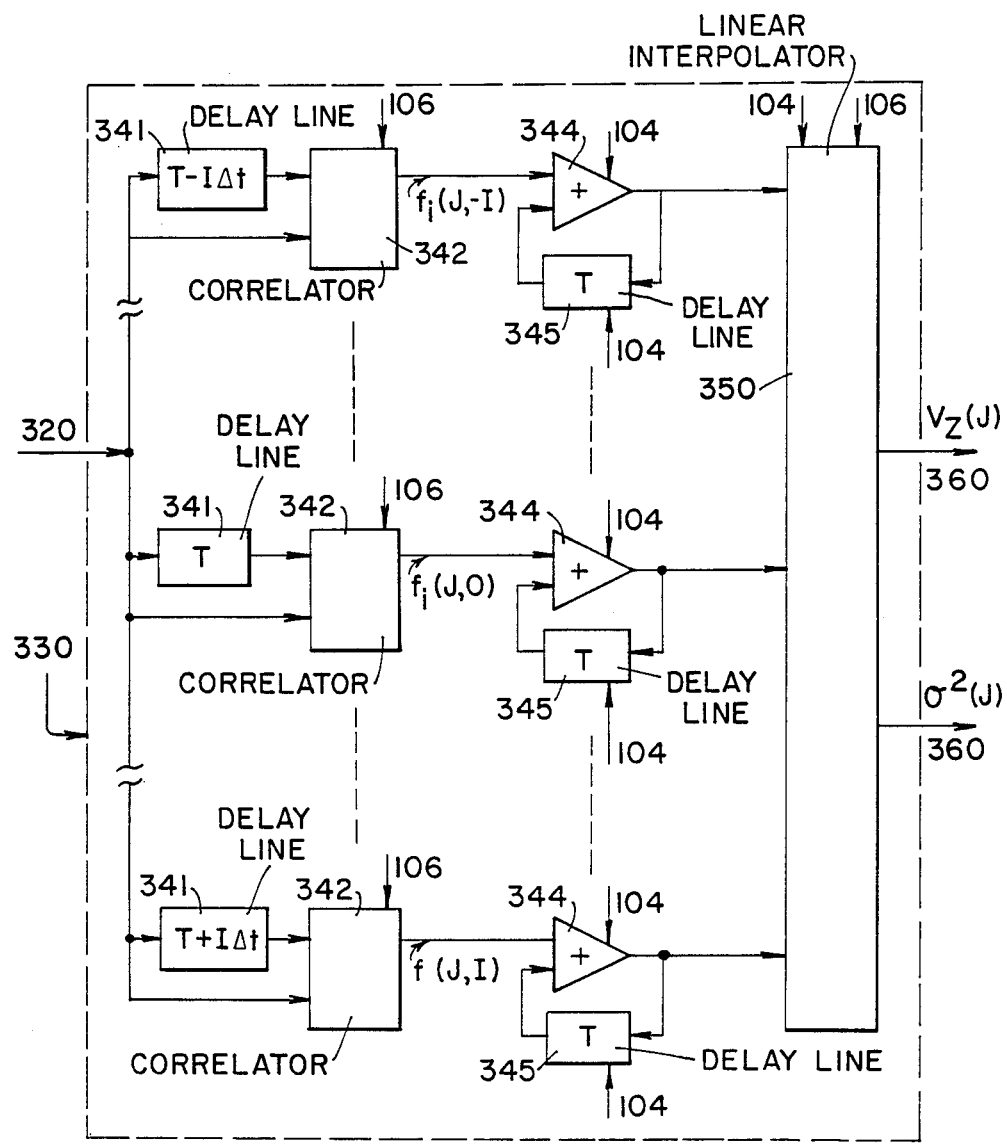
FIG. 13 is a 1-bit correlator of the prior art.
Figure 14:
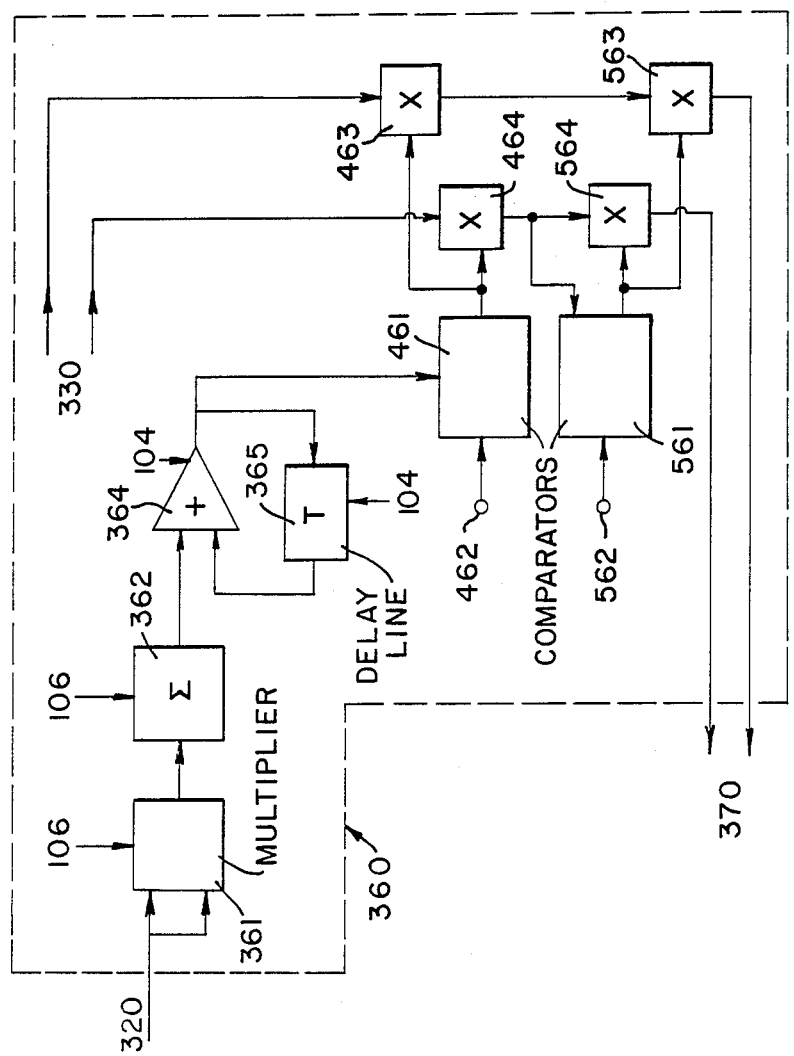
FIG. 14 is a discriminator of the prior art.

Although the present invention has been described as a cascade fractional step delay interpolation filters followed by 1-bit correlation estimators, it is also possible to construct the fractional step correlator in a manner similar to that indicated in the prior art FIG. 13 with fractional step interpolation filters acting on the output of correlation estimators.

What is claimed:

1. A fractional step correlator circuit for determining the cross-correlation of a first input signal and a second input signal, said input signals each being represented as a series of discrete digital samples having a sample period $\pi$, comprising:

a plurality of fractional step delay (FSD) digital interpolation filter means, each of said filter means functioning to interpolate the value of a filter input signal at a different predetermined time between discrete signal sample times, and a plurality of discrete time correlator circuits connected in cascade with said interpolation filters.

2. The fractional step correlator circuit of claim 1 wherein said first input signal is applied to a first input of each of said discrete time correlator circuits, said second input signal is applied to the input of each of said FSD interpolation filter means, and the output of each of said FSD filters are applied to second inputs of corresponding ones of said discrete time correlator circuits.

3. A circuit for determining the cross-correlation between a first input signal and a second input signal, said input signals each being represented as a series of discrete digital signal samples with sample period $\pi$, comprising:

first fixed delay means, having a delay period $K\pi$, said first input signal being applied to the input of said first delay means;

second fixed delay means having a delay period $K\pi$, said second input signal being connected to the input of said second delay means;

a plurality of fractional step delay (FSD) interpolation filter means, each of said interpolation filter means being connected to receive samples of said second input signal and to generate an estimate of the value of said second signal at a different time between the discrete samples times of said signal, so that each of said FSD filters estimates the value of said second signal at a separate time between said discrete sample times; and a plurality of discrete time correlator circuits, each having a first input connected to receive delayed samples of the first signal from the output of said first fixed delay means and having a second input connected to receive one of the estimates of the value of said second signal from a corresponding output of either said second delay means or one of said interpolation filters, to generate therefrom an estimate of the cross-correlation between the inputs supplied to said first and second inputs.

4. The circuit of claims 1, 2 or 3 wherein said discrete time correlator circuits are one-bit correlators.

5. The circuit of claims 2 or 3 wherein the interpolation filter means comprise a plurality of fractional step delay interpolation filters which are constructed to interpolate the value of said second input signal at a set of intervals which are fractions of the sample period $\pi$ after said discrete sample times of said second signal.

6. The circuit of claim 5 comprising N-1 fractional step delay interpolation filters which are constructed to interpolate the value of said second input signal at intervals of $(k\pi/N)$ after said discrete sample times of said second signal where N is an integer greater than 1 and $k=1, 2, 3, \ldots$ N-1.

7. The circuit of claim 6 wherein N=4.

* * * * *